United States Patent
Kavanagh et al.

(10) Patent No.: US 9,670,335 B2
(45) Date of Patent: Jun. 6, 2017

(54) COMPOSITIONS CONTAINING TETRAHYDROFURFURYL AND/OR ALKYL-SUBSTITUTED TETRAHYDROFURFURYL ESTERS OF CITRIC ACID

(71) Applicant: 3M INNOVATIVE PROPERTIES COMPANY, St. Paul, MN (US)

(72) Inventors: Maureen A. Kavanagh, Stanchfield, MN (US); Kevin M. Lewandowski, Inver Grove Heights, MN (US)

(73) Assignee: 3M INNOVATIVE PROPERTIES COMPANY, St. Paul, MN (US)

(*) Notice: Subject to any disclaimer, the term of this patent is extended or adjusted under 35 U.S.C. 154(b) by 23 days.

(21) Appl. No.: 14/387,596

(22) PCT Filed: Mar. 14, 2013

(86) PCT No.: PCT/US2013/031438
§ 371 (c)(1),
(2) Date: Sep. 24, 2014

(87) PCT Pub. No.: WO2013/148255
PCT Pub. Date: Oct. 3, 2013

(65) Prior Publication Data
US 2015/0033985 A1  Feb. 5, 2015

Related U.S. Application Data

(60) Provisional application No. 61/618,030, filed on Mar. 30, 2012.

(51) Int. Cl.
*C08K 5/00* (2006.01)
*C08K 5/1535* (2006.01)
*C07D 405/14* (2006.01)
*C07D 405/12* (2006.01)
*C07D 307/12* (2006.01)
*C08K 5/11* (2006.01)

(52) U.S. Cl.
CPC .......... *C08K 5/1535* (2013.01); *C07D 307/12* (2013.01); *C07D 405/12* (2013.01); *C07D 405/14* (2013.01); *C08K 5/11* (2013.01)

(58) Field of Classification Search
CPC ...... C08K 5/11; C08K 5/1535; C07D 307/12; C07D 405/12; C07D 405/14
See application file for complete search history.

(56) References Cited

U.S. PATENT DOCUMENTS

| | | |
|---|---|---|
| 4,710,532 A | 12/1987 | Hull |
| 4,711,922 A | 12/1987 | Hull |
| 4,789,700 A | 12/1988 | Hull |
| 4,824,893 A | 4/1989 | Hull |
| 4,870,204 A | 9/1989 | Hull |
| 4,883,905 A | 11/1989 | Hull |
| 4,892,967 A | 1/1990 | Hull |
| 4,931,583 A | 6/1990 | Hull |
| 4,954,649 A | 9/1990 | Hull |
| 4,972,036 A | 11/1990 | Elmore |
| 5,026,347 A | 6/1991 | Patel |
| 5,055,609 A | 10/1991 | Hull |
| 5,102,926 A | 4/1992 | Ross |
| 6,395,810 B1 | 5/2002 | Luitjes |
| 6,403,825 B1 | 6/2002 | Frappier |
| 2,772,776 A1 | 1/2003 | Bussi |
| 6,977,275 B2 | 12/2005 | Buchanan |
| 7,166,654 B2 | 1/2007 | Fujita |
| 7,276,546 B2 | 10/2007 | Buchanan |
| 7,863,343 B2 | 1/2011 | Haraguchi |
| 2005/0272843 A1 | 12/2005 | Kobayashi |
| 2006/0094894 A1 | 5/2006 | Day |
| 2011/0046283 A1 | 2/2011 | Grass |
| 2011/0272174 A1 | 11/2011 | Chaudhary |
| 2011/0287206 A1 | 11/2011 | Suwa |

FOREIGN PATENT DOCUMENTS

| | | |
|---|---|---|
| GB | 805587 | 12/1958 |
| JP | S 41-003189 | 2/1966 |
| JP | 2003-082158 | 3/2003 |
| WO | 2011/082052 | 7/2011 |

OTHER PUBLICATIONS

Belmares, "Hildebrand and Hansen Solubility Parameters from Molecular Dynamics with Applications to Electronic Nose Polymer Sensors", Journal of Computational Chemistry, Nov. 30, 2004, vol. 25, No. 15, pp. 1814-1826.
Brown, "Plasticizers from Tetrahydrofurfuryl Alcohol", Journal of Chemical and Engineering Data, Jan. 1960, vol. 5, No. 1, pp. 56-58.
Cadogan, D. F. and Howick, C. J. 2000. Plasticizers. Kirk-Othmer Encyclopedia of Chemical Technology. (30 pages).
Hoydonckx, H. E., Van Rhijn, W. M., Van Rhijn, W., De Vos, D. E. and Jacobs, P. A. 2007. Furfural and Derivatives. Ullmann's Encyclopedia of Industrial Chemistry. (pp. 285-313).
Karst, "Using the Solubility Parameter to Explain Disperse Dye Sorption on Polylactide", Journal of Applied Polymer Science, Apr. 15, 2005, vol. 96, No. 2, pp. 416-422.
Severs, "Flow Properties of Vinyl Chloride Resin Plastisols", Industrial and Engineering Chemistry, Nov. 1954, vol. 46, No. 11, pp. 2369-2375.

(Continued)

*Primary Examiner* — Alexander Polyansky
(74) *Attorney, Agent, or Firm* — Jean A. Lown

(57) ABSTRACT

Compositions containing tetrahydrofurfuryl and/or alkyl-substituted tetrahydrofurfuryl esters of citric acid are provided. These esters of citric acid can be formed from renewable materials and can be used, for example, as plasticizers for various polymeric materials. The tetrahydrofurfuryl and/or alkyl-substituted tetrahydrofurfuryl esters of citric acid typically have a low odor, have good compatibility with a variety of polymeric materials, and can be used at temperatures often encountered during hot melt processing of polymeric materials.

16 Claims, No Drawings

(56) References Cited

OTHER PUBLICATIONS

Wragg, "The Preparation of Tetrahydrofurfuryl Esters of Certain Mono- and Di-basic Carboxylic Acids", Journal of Chemical Society (Resumed), 1965, pp. 7162-7165.
International Search Report for PCT International Application No. PCT/US2013/031438, mailed on Jun. 19, 2013, 4pgs.

COMPOSITIONS CONTAINING TETRAHYDROFURFURYL AND/OR ALKYL-SUBSTITUTED TETRAHYDROFURFURYL ESTERS OF CITRIC ACID

CROSS REFERENCE TO RELATED APPLICATIONS

This application is a national stage filing under 35 U.S.C. 371 of PCT/US2013/031438, filed Mar. 14, 2013, which claims priority to U.S. Provisional Application No. 61/618,030, filed Mar. 30, 2012, the disclosure of which is incorporated by reference in its/their entirety herein.

TECHNICAL FIELD

Compositions and articles containing one or more tetrahydrofurfuryl and/or alkyl-substituted tetrahydrofurfuryl esters of citric acid are provided.

BACKGROUND

Various esters of citric acid are known and have been used as plasticizers for various polymeric materials as described, for example, in PCT Patent Application Publications WO 2011/082052 (Myers et al.), U.S. Patent Application Publication 2011/0046283 (Grass et al.), and U.S. Pat. No. 4,710,532 (Hull et al.), U.S. Pat. No. 5,026,347 (Patel), U.S. Pat. No. 6,403,825 (Frappier et al.), U.S. Pat. No. 5,102,926 (Ross et al.) and U.S. Pat. No. 7,166,654 (Fujita et al.). These esters are typically prepared from citric acid and petroleum based alcohols.

SUMMARY

Compositions are provided that include a tetrahydrofurfuryl ester of citric acid, an alkyl-substituted tetrahydrofurfuryl ester of citric acid, or both. The tetrahydrofurfuryl and/or alkyl-substituted tetrahydrofurfuryl esters of citric acid can be formed from renewable resources and can be used, for example, as plasticizers for various polymeric materials. The tetrahydrofurfuryl and/or alkyl-substituted tetrahydrofurfuryl esters of citric acid typically have a low odor, have good compatibility with a variety of polymeric materials such as hydrophilic polymeric materials, and can be used at temperatures often encountered during hot melt processing of polymeric materials.

In a first aspect, a composition is provided that contains at least two different citrate esters of Formula (I).

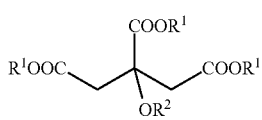

In Formula (I), each $R^1$ group is an alkyl, tetrahydrofurfuryl, or alkyl-substituted tetrahydrofurfuryl, wherein at least one $R^1$ is a tetrahydrofurfuryl or alkyl-substituted tetrahydrofurfuryl group. The $R^2$ group is hydrogen or an acyl.

In a second aspect, a composition is provided that contains (a) at least one citrate ester of Formula (I)

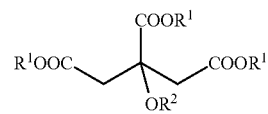

and at least one citrate ester of Formula (II).

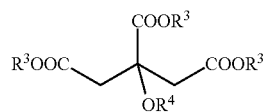

In Formula (I), each $R^1$ group is an alkyl, tetrahydrofurfuryl, or alkyl-substituted tetrahydrofurfuryl, wherein at least one $R^1$ is a tetrahydrofurfuryl or alkyl-substituted tetrahydrofurfuryl group. The $R^2$ group is hydrogen or an acyl. In Formula (II), each $R^3$ group is an alkyl and the $R^4$ group is hydrogen or an acyl.

In a third aspect, a composition is provided that contains at least one citrate ester of Formula (III).

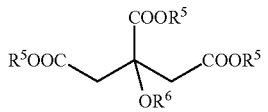

In Formula (III), each $R^5$ group is a tetrahydrofurfuryl or alkyl-substituted tetrahydrofurfuryl group. The $R^6$ group is hydrogen or an acyl.

DETAILED DESCRIPTION

Compositions are provided that include at least one tetrahydrofurfuryl and/or alkyl-substituted tetrahydrofurfuryl ester of citric acid. These esters of citric acid can be formed by reacting citric acid with tetrahydrofurfuryl alcohol and/or alkyl-substituted tetrahydrofurfuryl alcohol. Both the citric acid and the alcohol can be plant-based materials (i.e., renewable materials). The tetrahydrofurfuryl and/or alkyl-substituted tetrahydrofurfuryl esters of citric acid are compatible with a variety of polymeric materials such as those that are hydrophilic and can function as plasticizers for the polymeric materials.

The terms "a", "an", "the", "at least one", and "one or more" are used interchangeably.

The term "and/or" means one or both such as in the expression A and/or B refers to A alone, B alone, or to both A and B.

The term "alkyl" refers to a monovalent radical of an alkane. Suitable alkyl groups can have up to 20 carbon atoms, up to 16 carbon atoms, up to 12 carbon atoms, up to 10 carbon atoms, up to 8 carbon atoms, up to 6 carbon atoms, up to 4 carbon atoms, or up to 3 carbon atoms. The alkyl groups can be linear, branched, cyclic, or a combination thereof. Linear alkyl groups often have 1 to 20 carbon atoms, 1 to 10 carbon atoms, 1 to 6 carbon atoms, or 1 to 4 carbon atoms. Branched alkyl groups often have 3 to 20 carbon atoms, 3 to 10 carbon atoms, or 3 to 6 carbon atoms. Cyclic alkyl groups often have 3 to 20 carbon atoms, 5 to 20 carbon atoms, 6 to 20 carbon atoms, 5 to 10 carbon atoms, or 6 to 10 carbon atoms.

The term "acyl" refers to a monovalent group of formula —(CO)R$^a$ where R$^a$ is an alkyl group and (CO) denotes a carbonyl group (i.e., a carbon atom attached to an oxygen atom with a double bond). The alkyl group R$^a$ often has 1 to 10 carbon atoms, 1 to 6 carbon atoms, 1 to 4 carbon atoms, or 1 to 3 carbon atoms. One example acyl group is an acetyl group —(CO)CH$_3$.

The term "tetrahydrofurfuryl group" refers to a 2-tetrahydrofurfuryl group

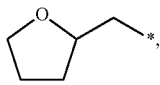

to a 3-tetrahydrofurfuryl group

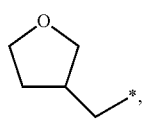

or to both the 2-tetrahydrofurfuryl group and the 3-tetrahydrofurfuryl group. The asterisk symbol denotes that attachment site of the tetrahydrofurfuryl group to the rest of the citrate ester compound.

The term "alkyl-substituted tetrahydrofurfuryl" group refers to either a 2-tetrahydrofurfuryl group or 3-tetrahydrofurfurtyl group that is substituted with at least one alkyl group. The number of alkyl substituents is often in the range of 1 to 3. Suitable alkyl substituents for the tetrahydrofurfuryl group often have 1 to 10 carbon atoms, 1 to 6 carbon atoms, 1 to 4 carbon atoms, or 1 to 3 carbon atoms. The alkyl can be positioned on any suitable carbon atom of the 5-membered ring but is often at the 4-position or the 5-position. In some embodiments, the alkyl substituent is methyl such as in 5-methyl-2-tetrahydrofurfuryl.

The term "THF group" can be used to refer to a tetrahydrofurfuryl group, an alkyl-substituted tetrahydrofurfuryl group, or to both.

The term "THF-citrate ester" refers to citrate esters having one, two, or three tetrahydrofurfuryl groups, alkyl-substituted tetrahydrofurfuryl groups, or a combination thereof.

The term "alkyl ester of citric acid" is used interchangeably with the term "tri(alkyl)-citrate ester" and refers to citrate esters having three alkyl groups. More specifically, the compound is a citrate ester having three groups of formula —(CO)OR$^a$ where R$^a$ is an alkyl group. The alkyl group can have up to 20 carbon atoms, up to 16 carbon atoms, up to 12 carbon atoms, up to 10 carbon atoms, up to 8 carbon atoms, up to 6 carbon atoms, up to 4 carbon atoms, or up to 3 carbon atoms. The alkyl groups can be linear, branched, cyclic, or a combination thereof.

The term "citrate ester" refers to (a) one or more THF-citrate esters plus (b) any optional tri(alkyl)-citrate ester that may be present.

The term "polymeric material" refers to any homopolymer, copolymer, terpolymer, and the like.

In a first aspect, a composition is provided that contains at least two different THF-citrate esters of Formula (I).

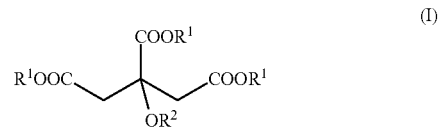

(I)

In Formula (I), each R$^1$ group is an alkyl, tetrahydrofurfuryl, or alkyl-substituted tetrahydrofurfuryl, wherein at least one R$^1$ is a tetrahydrofurfuryl or alkyl-substituted tetrahydrofurfuryl group. The R$^2$ group is hydrogen or an acyl. The alkyl, tetrahydrofurfuryl, alkyl-substituted tetrahydrofurfuryl, and acyl groups are the same as defined above.

A THF-citrate ester with a single THF group (i.e., a tetrahydrofurfuryl group and/or an alkyl-substituted tetrahydrofurfuryl group) can be referred to as a mono(THF)-di(alkyl)-citrate ester. A mono(THF)-di(alkyl)-citrate ester has one R$^1$ group equal to THF (i.e., one R$^1$ group in Formula (I) is a tetrahydrofurfuryl group and/or an alkyl-substituted tetrahydrofurfuryl group) and two R$^1$ groups equal to an alkyl. A THF-citrate ester with two THF groups can be referred to as a di(THF)-mono(alkyl)-citrate ester. A di(THF)-mono(alkyl)-citrate ester has two R$^1$ groups equal to THF and one R$^1$ group equal to an alkyl. A THF-citrate ester with three THF groups can be referred to as a tri(THF)-citrate ester. A tri(THF)-citrate ester has three R$^1$ groups equal to THF groups.

In this first aspect, the compositions contain at least two different THF-citrate esters. A mono(THF)-di(alkyl)-citrate ester can be combined with a di(THF)-mono(alkyl)-citrate ester, with a tri(THF)-citrate ester, or with both. Similarly, a di(THF)-mono(alkyl)citrate ester can be combined with a mono(THF)-di(alkyl)-citrate ester, with a tri(THF)-citrate ester, or with both.

Compositions having at least two different THF-citrate of Formula (I) can contain 1 to 75 weight percent mono(THF)-di(alkyl)-citrate ester, 1 to 75 weight percent di(THF)-mono(alkyl)-citrate ester, and 1 to 75 weight percent tri(THF)-citrate ester. Some specific compositions having at least two different THF-citrate esters of Formula (I) contain 1 to 50 weight percent mono(THF)-di(alkyl)-citrate ester, 10 to 75 weight percent di(THF)-mono(alkyl)-citrate ester, and 1 to 50 weight percent tri(THF)-citrate ester. More specific compositions contain 10 to 50 weight percent mono(THF)-di(alkyl)-citrate ester, 30 to 70 weight percent di(THF)-mono(alkyl)-citrate ester, and 10 to 50 weight percent tri(THF)-citrate ester. Some even more specific compositions contain 15 to 35 weight percent mono(THF)-di(alkyl)-citrate ester, 35 to 65 weight percent di(THF)-mono(alkyl)-citrate ester, and 15 to 35 weight percent tri(THF)-citrate ester. The weight percent values are based on the total weight of citrate esters in the composition (i.e., citrate esters having at least one THF group plus any other citrate esters that may be present such as tri(alkyl)-citrate esters).

In a second aspect, a composition is provided that contains (a) at least one THF-citrate ester of Formula (I)

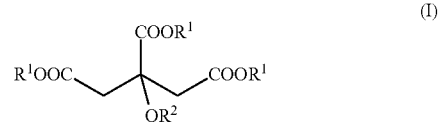

(I)

and at least one tri(alkyl)-citrate ester of Formula (II).

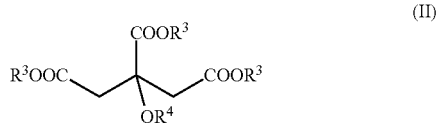

(II)

In Formula (I), each $R^1$ group is an alkyl, tetrahydrofurfuryl, or alkyl-substituted tetrahydrofurfuryl. At least one of the $R^1$ groups is a tetrahydrofurfuryl or alkyl-substituted tetrahydrofurfuryl group. The $R^2$ group is hydrogen or an acyl. In Formula (II), each $R^3$ group is an alkyl and the $R^4$ group is hydrogen or an acyl. The alkyl, tetrahydrofurfuryl, alkyl-substituted tetrahydrofurfuryl, and acyl groups are the same as defined above.

In this aspect, the tri(alkyl)-citrate ester of Formula (II) can be combined with at least one THF-citrate ester of Formula (I). That is, the tri(alkyl)-citrate ester can be combined with a mono(THF)-di(alkyl)-citrate ester, with a di(THF)-mono(alkyl)-citrate ester, with a tri(THF)-citrate ester, or with a combination thereof.

Some specific compositions contain 0.5 to 75 weight percent tri(alkyl)-citrate ester of Formula (II) and 25 to 99.5 weight percent THF-citrate ester of Formula (I). Some more specific compositions contain 1 to 60 weight percent tri(alkyl)-citrate ester and 40 to 99 weight percent THF-citrate ester. Some even more specific compositions contain 10 to 60 weight percent tri(alkyl)-citrate ester and 40 to 90 weight percent THF-citrate esters, or 10 to 40 weight percent tri(alkyl)-citrate ester and 60 to 90 weight percent THF-citrate esters. The weight percent values are based on the total weight of citrate esters in the composition.

In some embodiments of the second aspect, the tri(alkyl)-citrate ester is mixed with a tri(THF)-citrate ester. Some such compositions contain 10 to 90 weight percent tri(THF)-citrate ester and 10 to 90 weight percent tri(alkyl)-citrate ester. Some more specific compositions contain 20 to 80 weight percent tri(THF)-citrate ester and 20 to 80 weight percent tri(alkyl)-citrate ester. Some more specific compositions contain 40 to 60 weight percent tri(THF)-citrate esters and 40 to 60 weight percent tri(alkyl)-citrate esters. Although the THF-citrate esters in these embodiments is predominately tri(THF)-citrate ester, any of the compositions can contain 0 to 10 weight percent di(THF)-mono(alkyl)-citrate ester, mono(THF)-di(alkyl)-citrate esters, or a combination thereof. The weight percent values are based on the total weight of citrate esters in the composition.

In other embodiments of the second aspect, the compositions contain a mixture of different THF-citrate esters. Some such compositions contain 0 to 50 weight percent tri(THF)-citrate ester, 1 to 75 weight percent di(THF)-mono(alkyl)-citrate ester, 5 to 75 weight percent mono(THF)-di(alkyl)-citrate ester, and 0.5 to 75 weight percent tri(alkyl)-citrate ester. Some more specific compositions contain 1 to 40 weight percent tri(THF)-citrate ester, 5 to 60 weight percent di(THF)-mono(alkyl)-citrate ester, 10 to 60 weight percent mono(THF)-di(alkyl)-citrate ester, and 1 to 60 weight percent tri(alkyl)-citrate ester. Some even more specific compositions contain 1 to 30 weight percent tri(THF)-citrate ester, 10 to 60 weight percent di(THF)-mono(alkyl)-citrate ester, 20 to 60 weight percent mono(THF)-di(alkyl)-citrate ester, and 1 to 50 weight percent tri(alkyl)-citrate ester. Still other compositions contain 1 to 20 weight percent tri(THF)-citrate ester, 10 to 40 weight percent di(THF)-mono(alkyl)-citrate ester, 20 to 60 weight percent mono(THF)-di(alkyl)-citrate ester, and 1 to 40 weight percent tri(alkyl)-citrate ester. The weight percent values are based on the total weight of citrate esters in the composition.

In a third aspect, a composition is provided that contains at least one tri(THF)-citrate ester of Formula (III).

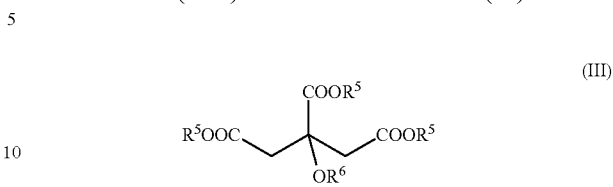

(III)

In Formula (III), each $R^5$ group is a tetrahydrofurfuryl or alkyl-substituted tetrahydrofurfuryl group. The $R^6$ group is hydrogen or an acyl. The tetrahydrofurfuryl, alkyl-substituted tetrahydrofurfuryl, and acyl groups are the same as defined above.

The tri(THF)-citrate esters of Formula (III) can be used alone (e.g., as the only citrate ester in the composition) or can be combined with one of more THF-citrate esters of Formula (I) that is not a tri(THF)-citrate ester and/or one or more tri(alkyl)-citrate esters of Formula (II). In some embodiments, the tri(THF)-citrate ester is the only citrate ester in the composition. In other embodiments, the tri(THF)-citrate ester is the only THF-citrate ester in the composition but is combined with at least one tri(alkyl)-citrate ester of Formula (II). Such compositions can contain 10 to 90 weight percent tri(THF)-citrate ester of Formula (III) and 10 to 90 weight percent tri(alkyl)-citrate ester of Formula (II), 20 to 80 weight percent tri(THF)-citrate ester of Formula (III) and 20 to 80 weight percent tri(alkyl)-citrate ester of Formula (II), or 40 to 60 weight percent tri(THF)-citrate ester of Formula (III) and 40 to 60 weight percent tri(alkyl)-citrate ester of Formula (II).

The various THF-citrate esters of Formula (I) or Formula (III) and the various tri(alkyl)-citrate esters of Formula (II) can be prepared by reacting an alcohol with citric acid in the presence of a strong acid catalyst. Strong acid catalysts include, but are not limited to, sulfuric acid, p-toluene sulfonic acid, methanesulfonic acid, and a mixture thereof. This reaction is often performed under reflux conditions or at a temperature in the range of about 80° C. to 160° C. An organic solvent such as heptane, toluene, or the like is often included in the reaction mixture. Depending on the desired reaction product, the alcohol is a THF alcohol (i.e., $R^bOH$ is a tetrahydrofurfuryl alcohol, an alkyl-substituted tetrahydrofurfuryl alcohol, or a mixture thereof), an alkyl alcohol (i.e., an alcohol of formula $R^bOH$ where $R^b$ is an alkyl as defined above), or a mixture thereof. The reaction is shown in Reaction Scheme A.

Reaction Scheme A

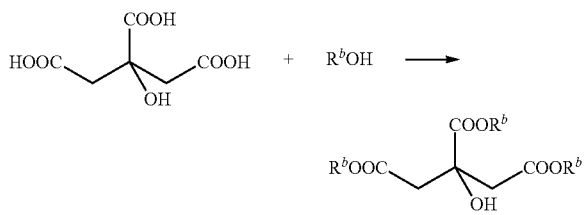

Tri(THF)-citrate ester can be prepared using a tetrahydrofurfuryl alcohol (i.e., tetrahydrofuran-2-methanol or tetrahydrofuran-3-methanol) or an alkyl-substituted tetrahydrofurfuryl alcohol (e.g., 5-methyl-tetrahydrofuran-2- methanol). Greater than 3 moles of tetrahydrofurfuryl alcohol per mole of citric acid is often used for complete conversion to the tri(THF)-citrate ester.

As an alternative to Reaction Scheme A, the various THF-citrate esters of Formula (I) can also be prepared by a trans-esterification of a tri(alkyl)-citrate esters of Formula (III) with tetrahydrofurfuryl alcohol and/or alkyl-substituted tetrahydrofurfuryl alcohol. For example, tri(methyl)-citrate ester or tri(ethyl)-citrate ester can be trans-esterified with the alcohol $R^bOH$ where $R^b$ is a tetrahydrofurfuryl or alkyl-substituted furfuryl.

Tri(alkyl)-citrate esters can be prepared using an alkyl alcohol. Greater than 3 moles of alkyl alcohol per mole of citric acid is often used to achieve complete conversion to the tri(alkyl)-citrate ester. Some tri(alkyl)-citrate esters are commercially available, for example, under the trade designation CITROFLEX from Vertellus Specialties, Inc. (Greensboro, N.C., USA).

Mono(THF)-di(alkyl)-citrate esters and di(THF)-mono (alkyl)-citrate esters can be prepared using a THF alcohol (i.e., a tetrahydrofurfuryl alcohol and/or alkyl-substituted tetrahydrofurfuryl alcohol) in combination with an alkyl alcohol. The amount of the alkyl alcohol relative to the amount of THF alcohol can be varied to produce different mixtures of citrate esters. The product often contains a mixture of both mono(THF)-di(alkyl)-citrate ester and di(THF)-mono(alkyl)-citrate esters. Additionally, the product often includes at least some tri(alkyl)-citrate ester and at least some tri(THF)-citrate ester.

Both the citric acid and the THF alcohol can be formed from renewable materials. Citric acid is often produced by various molds (e.g., *Aspergillus niger*) from sugar. THF alcohol can be formed from C5 sugars (i.e., sugars having 5 carbon atoms). The C5 sugars can be dehydrated to furfural (i.e., 2-furaldehyde or furfuraldehyde), which can be hydrogenated to furfuryl alcohol. Furfuryl alcohol can be further hydrogenated with a nickel catalyst to tetrahydrofurfuryl alcohol. Methods of preparing tetrahydrofurfuryl alcohol are further described in the reference Hoydonckx et al., Furfural and Derivatives, *Ullmann's Encyclopedia of Industrial Chemistry*, Wiley-VCH Verlag GmbH & Co., pp. 285-313 (2012).

The various THF-citrate esters or the tri(alkyl)-citrate ester can be further reacted as shown in Reaction Scheme B to replace the hydroxyl group with an acyloxy group. The added reactant can be an alkyl carboxylic acid ($R^c$—(CO) OH as shown), an alkyl anhydride ($R^c$—(CO)O(CO)—$R^c$), or an alkyl acid chloride ($R^c$—(CO)Cl) where $R^c$ is an alkyl. The alkyl group can have up to 20 carbon atoms, up to 16 carbon atoms, up to 12 carbon atoms, up to 10 carbon atoms, up to 8 carbon atoms, up to 6 carbon atoms, up to 4 carbon atoms, or up to 3 carbon atoms. The alkyl groups can be linear, branched, cyclic, or a combination thereof. This reaction is often performed at a temperature in the range of about 80° C. to 120° C.

Reaction Scheme B

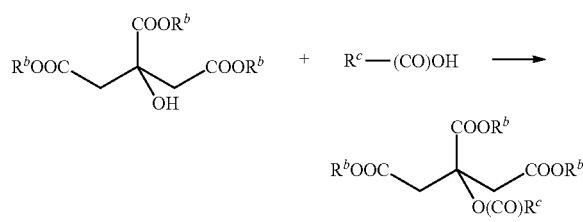

Any of the compositions can further include a polymeric material. Suitable polymeric materials are selected to be compatible with (i.e., miscible with) the compositions that include one or more THF-citrate esters. Compatibility can be determined, for example, by measuring the haze of a film prepared from a mixture of the polymeric material and THF-citrate ester. One suitable method of measuring haze is described in Test Method 3 (Measurement of Total Transmittance, Haze, and Clarity) included in the Example section. A low haze value (e.g., less than 5, less than 4, less than 3, less than 2, or less than 1) is typically associated with a mixture having compatible components.

The THF-citrate esters are typically considered to be compatible with a polymeric material if the THF-citrate esters are soluble in the polymeric material. Compatibility of the polymeric material and the THF-citrate esters can also be determined through calculation of the solubility parameter of the polymeric material and the THF-citrate ester. The closer the solubility parameters of the two materials, the more likely these materials are to be compatible. Solubility parameters can be calculated using the general procedures described in the article by Belmares et al., *J. Comp. Chem.*, 24 (15), 1813 (2004) and that is implemented in software commercially available under the trade designation CULGI from Culgi Software (Leiden, The Netherlands). The solubility parameter of the various THF-citrate esters are often in the range of 7 to 13 $cal^{0.5}/cm^{1.5}$, in the range of 8 to 12 $cal^{0.5}/cm^{1.5}$, or in the range of 9 to 12 $cal^{0.5}/cm^{1.5}$. The solubility parameter of the THF-citrate ester can be matched as well as or better than tri(alkyl)-citrate esters with various materials such as polylactic acid.

Suitable polymeric materials for combination with the THF-citrate esters are typically hydrophilic. Example polymeric materials include various thermoplastic polymers such as various aliphatic polyesters (e.g., polylactic acid), cellulose esters, polyvinyl chloride, and various acrylic polymers such as poly(methyl methacrylate). Other example polymeric materials include various elastomeric polymers such as those included in adhesive compositions. The elastomeric polymers are often acrylic polymers such as polymers formed using at least one alkyl(meth)acrylate and optionally a polar monomer such as (meth)acrylic acid.

The aliphatic polyesters can be formed by dehydration-polycondensation reactions of one or more aliphatic hydroxycarboxylic acids. Example hydroxycarboxylic acids include, but are not limited to, L-lactic acid, D-lactic acid, glycolic acid, 3-hydroxypropanic acid, 3-hydroxybutyric acid, 4-hydroxybutyric acid, 4-hydroxypentanoic acid, 3-hydroxypentanoic, 5-hydroxypentanoic acid, 3-hydroxyhexanoic acid, 6-hydroxyhexanoic acid, 3-hydroxyheptanoic, 3-hydroxyoctanoic acid, or mixtures thereof.

Alternatively, the aliphatic polyesters can be formed by dehydration-polycondensation reactions of a mixture containing an aliphatic polycarboxylic acid (i.e., a compound having two or more carboxylic acid groups) and an aliphatic polyol (i.e., a compound having two or more hydroxyl groups). Examples of polycarboxylic acids include, but are not limited to, oxalic acid, succinic acid, malonic acid, glutaric acid, adipic acid, pimelic acid, suberic acid, azelaic acid, undecanedioic acid, dodecanedioic acid, and anhydrides thereof. Examples of polyols include, but are not limited to, ethylene glycol, diethylene glycol, triethylene glycol, polyethylene glycol, polypropylene glycol, 1,3-propanediol, 1,2-propanediol, dipropylene glycol, 1,2-butanediol, 1,3-butanediol, 1,4-butanediol, 3-methyl-1,5-pentanediol, 1,6-hexanediol, 1,9-nonanediol, neopentyl glycol, tetramethylene glycol and 1,4-cyclohexanedimethanol. Suitable polycarboxylic acids often have two carboxylic acid group and suitable polyols often have two hydroxyl groups.

The aliphatic polyester can be a polylactic acid based resin (PLA-based resin). Some example PLA-based resins can be formed from L-lactic acid, D-lactic acid, or a mixture thereof. Other example PLA-based resins can be prepared from L-lactic acid, D-lactic acid, or a mixture thereof in combination with at least one aliphatic hydroxycarboxylic acid (other than lactic acid). Yet other PLA-based resins are copolymers prepared from L-lactide, D-lactide, or a mixture thereof. The lactides are cyclic dimmers of lactic acid that can be subjected to a ring-opening polymerization reaction in the presence of a compound having a hydroxyl group such as a hydroxycarboxylic acid. Suitable hydroxycarboxylic acids include, but are not limited to, glycolic acid, 3-hydroxypropanic acid, 3-hydroxybutyric acid, 4-hydroxybutyric acid, 4-hydropentanoic acid, 3-hydroxypentanoic, 5-hydroxypentanoic acid, 3-hydroxyhexanoic acid, 6-hydroxyhexanoic acid, 3-hydroxyheptanoic, 3-hydroxyoctanoic acid, or mixtures thereof. Example hydroxycarboxylic acids are the same as those listed above. In one more specific example, the PLA-based resin is a copolymer of (1) L-lactic acid, D-lactic acid, or a mixture thereof plus (2) glycolic acid.

Other example PLA-based resins can prepared using a combination of (1) a lactic acid (e.g., D-lactic acid, L-lactic acid, or a mixture thereof), (2) an aliphatic polycarboxylic acid (i.e., a compound having at least two carboxylic acid groups), and (3) an aliphatic polyol (i.e., a compound having at least two hydroxyl groups). Yet other PLA-based resins can be prepared using a combination of (1) a lactide (e.g., D-lactide, L-lactide, or a mixture thereof), (2) an aliphatic polycarboxylic acid, and (3) an aliphatic polyol. Suitable polycarboxylic acids and polyols are the same as listed above.

PLA-based resins often contain lactic acid units (i.e., the residue of the lactic acid present in the polymeric material) and other optional units such as hydroxycarboxylic acid units (i.e., the residue of the hydroxycarboxylic acid present in the polymeric material), polycarboxylic acid units (i.e., the residue of the polycarboxylic acid present in the polymeric material), and polyol units (i.e., the residue of the polyol present in the polymeric material). These PLA-based resins often contain at least 50 weight percent lactic acid units. For example, the PLA-based resins can contain at least 60 weight percent, at least 70 weight percent, at least 80 weight percent, at least 90 weight percent, at least 95 weight percent, or at least 98 weight percent lactic acid units.

Suitable PLA-based resins are commercially available under the trade designation INGEO (e.g., INGEO 4032D, INGEO 4043D, and INGEO 4060D) from NatureWorks, LLC (Minnetonka, Minn., USA).

The PLA-based resin can be used as the only polymeric material in the composition or can be combined with another polymeric material such as another polyester resin, a polyolefin (e.g., polyethylene, polypropylene, or copolymers thereof), or the like. In many embodiments, at least 50 weight percent of the polymeric material is a PLA-based resin. For example, the polymeric material can include 50 to 95 weight percent PLA-based resin and 5 to 50 weight percent of another polyester and/or polyolefin, 60 to 95 weight percent PLA-based resin and 5 to 40 weight percent of another polyester and/or polyolefin, or 75 to 95 weight percent PLA-based resin and 5 to 25 weight percent of another polyester and/or polyolefin.

In other embodiments, the polymeric material is a cellulose ester (i.e., a reaction product of cellulose and a carboxylic acid). Example cellulose esters include cellulose acetate, cellulose triacetate, cellulose propionate, cellulose acetate propionate, cellulose tripropionate, cellulose butyrate, cellulose tributryrate, and cellulose acetate butyrate. The various cellulose esters can be prepared with differing solubility depending on the number of hydroxyl groups present. Various cellulose esters are commercially available from Eastman (Kingsport, Tenn., USA).

In yet other embodiments, the polymeric material is a polyvinyl chloride (PVC) resin. The polyvinyl chloride can be a polymerized to form a homopolymer or copolymer. Suitable co-monomers for formation of copolymers include, for example, ethylenically unsaturated olefins such as those having 2 to 10 carbon atoms or 2 to 6 carbon atoms (e.g., ethylene and propylene), vinyl esters of carboxylic acids such as carboxylic acids having 2 to 10 carbon atoms or 2 to 6 carbon atoms or 2 to 6 carbon atoms (e.g., vinyl acetate, vinyl proprionate, and 2-ethylhexanoic acid vinyl ester), vinyl halides (e.g., vinyl fluoride, vinylidene fluoride, and vinylidene chloride), vinyl ethers (e.g., vinyl methyl ether and vinyl butyl ether), vinyl pyridine, and unsaturated acids (e.g., maleic acid, fumaric acid).

PVC resins often contain at least 50 weight percent vinyl chloride units (i.e., the residue of the vinyl chloride monomer present in the polymeric material). For example, the polyvinyl chloride resin contains at least 60 weight percent, at least 70 weight percent, at least 80 weight percent, at least 90 weight percent, at least 95 weight percent, or at least 98 weight percent vinyl chloride residue.

PVC resins are commercially available under the trade designation OXYVINYLS from OxyChem (Dallas, Tex., USA), under the trade designation FORMOLON from Formosa Plastics (Livingston, N.J., USA), or under the trade designation GEON from PolyOne (Avon Lake, Ohio, USA).

In still another embodiment, the thermoplastic polymeric material is poly(methyl methacrylate) (PMMA) or a copolymer thereof. Copolymers are prepared from a mixture of methyl methacrylate and various optional monomers such as various alkyl(meth)acrylates and (meth)acrylic acid. PMMA is commercially available from under the trade designation ELVACITE from Lucite International (Memphis, Tenn., USA) and under the trade designation PLEXIGLAS from Arkema (Bristol, Pa., USA).

The compositions can be used to provide an adhesive composition. In such compositions, the polymeric material is an elastomeric material. The elastomeric material is often an acrylic polymer such as, for example, one formed using one or more alkyl(meth)acrylate monomers. The acrylic polymer is often a copolymer that if formed from one or more alkyl(meth)acrylate monomers and at least one polar monomer such as, for example, (meth)acrylic acid, hydroxy-substituted alkyl(meth)acrylate monomers, or mixtures thereof.

Any suitable molecular weight can be used for the polymeric material that is combined with the citrate ester. The weight average molecular weight is often at least 1,000 grams/mole, at least 10,000 grams/mole, at least 20,000 grams/mole, at least 50,000 grams/mole, at least 100,000 grams/mole, or at least 200,000 grams/mole. The weight average molecular weight can be up to 1 million grams/mole, up to 800,000 grams/mole, up to 600,000 grams/mole, up to 40,000 grams/mole. For example, the polymeric material can have a weight average molecular weight in a range of 10,000 grams/mole to 1 million grams/mole, in a range of 20,000 grams/mole to 600,000 grams/mole, in a range of 50,000 grams/mole to 500,000 grams/mole, or in a range of 10,000 grams/mole to 100,000 grams/mole.

The compositions containing one or more citrate esters (i.e., one or more THF-citrate ester plus any optional tri(alkyl)-citrate ester) can be used as plasticizers for the polymeric material. A plasticizer is often added to a polymeric material to make the polymeric material more flexible, softer, and more workable (i.e., easier to process). More specifically, the mixture resulting from the addition of the plasticizer to the polymeric material typically has a lower glass transition temperature compared to the polymeric material alone. The glass transition temperature of a polymeric material can be lowered, for example, by at least 30° C., at least 40° C., at least 50° C., at least 60° C., or at least 70° C. by the addition of one or more citrate esters. The temperature change (i.e., decrease) tends to correlate with the amount of plasticizer added to the polymeric material. It is the lowering of the glass transition temperature that usually leads to the increased flexibility, increased elongation, and increased workability.

In some embodiments, it is advantageous to include a plurality of citrate esters. A mixture of different citrate esters with the polymeric material can often provide a composition with a lower viscosity than compositions using only a tri(THF)-citrate ester of Formula (III). Stated differently, compositions containing two or more THF-citrate esters of Formula (I) or compositions containing a THF-citrate ester of Formula (I) plus a tri(alkyl)citrate ester of Formula (II) will often have a lower viscosity than compositions having a single tri(THF)-citrate ester of Formula (III). Additionally, compositions containing two or more THF-citrate esters of Formula (I) or compositions containing a THF-citrate ester of Formula (I) plus a tri(alkyl)citrate ester of Formula (II) will often have a higher elongation (i.e., elongation to break) than compositions having a single tri(THF)-citrate ester of Formula (III).

On the other hand, the tri(THF)-citrate esters of Formula (III) tend to have a higher boiling point that the mono(THF)-di(alkyl)-citrate esters and di(THF)-mono(alkyl)-citrate esters of Formula (II). That is, the use of the tri(THF)-citrate esters may enhance the age stability of the composition more than the other THF-citrate esters. Additionally, a mixture of a polymeric material and the tri(THF)-citrate esters can have a higher modulus compared to the mono(THF)-di(alkyl)-citrate esters and di(THF)-mono(alkyl)-citrate esters of Formula (II).

Because the effects of the tri(THF)-citrate ester, di(THF)-mono(alkyl)-citrate ester, and mono(THF)-di(alkyl)-citrate ester can vary, properties such as the elongation, modulus, glass transition temperature, and age stability can be varied by the selection of the one or more THF-citrate esters included in the composition. That is, depending on the particular application, the plasticizer can be selected to provide the desired properties.

Compositions that include both a polymeric material plus one or more citrate esters often contain at least 1 weight percent citrate ester based on a total weight of the composition. If the composition contains less than 1 weight percent or less than 5 weight percent citrate ester, the effect of the addition of the citrate ester may not be detected. For example, there may be no change or only a very small change in the glass transition temperature. The composition can include, for example, at least 5 weight percent, at least 10 weight percent, at least 15 weight percent, at least 20 weight percent, or at least 25 weight percent citrate ester. The amount of citrate ester in the composition can be up to 99 weight percent based on a total weight of the composition. The upper limit is often determined by the compatibility of the citrate ester with the polymeric material. Some example compositions can include up to 95 weight percent, up to 75 weight percent, up to 50 weight percent, up to 40 weight percent, up to 30 weight percent, or up to 20 weight percent citrate ester.

Compositions with a thermoplastic polymeric material can contain 1 to 95 weight percent citrate ester and 5 to 99 weight percent polymeric material based on a total weight of the composition. Some example compositions contain 5 to 95 weight percent citrate ester and 5 to 95 weight percent polymeric material, 5 to 75 weight percent citrate ester and 25 to 95 weight percent polymeric material, 5 to 50 weight percent citrate ester and 50 to 95 weight percent polymeric material, 5 to 30 weight percent citrate ester and 70 to 95 weight percent polymeric material, or 5 to 20 weight percent citrate ester and 80 to 95 weight percent polymeric material.

Compositions with an elastomeric polymeric material for use as an adhesive can contain 70 to 99 weight percent polymeric material and 1 to 30 weight percent citrate ester based on a total weight of the composition. Some example compositions contain 75 to 99 weight percent polymeric material and 1 to 25 weight percent citrate ester, 80 to 99 weight percent polymeric material and 1 to 20 weight percent citrate ester, or 80 to 95 weight percent polymeric material and 5 to 20 weight percent citrate ester.

Any other optional components can be added to the compositions. Such optional components include, but are not limited to, anti-blocking agents, anti-slip agents, fillers, nucleating agents, thermal stabilizers, light stabilizers, lubricants, pigments, colorants, anti-oxidants, anti-static agents, flame retardants, melt strength enhancers, impact modifiers, and the like. The use of any of these additional optional components may be desirable to provide compositions for specific applications.

Additionally, the various THF-citrate esters can be used in combination with one or more other types of plasticizers such as those that are petroleum-based (i.e., plasticizers that are not based on renewable materials). Some example plasticizers include various phthalate esters such as diethyl phthalate, diisobutyl phthalate, dibutyl phthalate, diisoheptyl phthalate, dioctyl phthalate, diisooctyl phthalate, dinonyl phthalate, diisononyl phthalate, diisodecyl phthalate, and benzylbutyl phthalate; various adipate esters such as di-2-ethylhexyl adipate, dioctyl adipate, diisononyl adipate, and diisodecyl adipate; various phosphate esters such as tri-2-ethylhexyl phosphate, 2-ethylhexyl diphenyl phosphate, trioctylphosphate, and tricresyl phosphate; various trimettitate esters such as tris-2-ethylhexyl trimettilate and trioctyl trimettilate; various sebacate and azelate esters; and various sulfonate esters. Other example plasticizers include polyester plasticizers that can be formed by a condensation reaction of propanediols or butanediols with adipic acid.

Any suitable method of mixing the polymeric material and the one or more citrate esters can be used such as dry mixing, melt mixing, or mixing in the presence of a suitable solvent (e.g., a solvent that dissolves both the polymeric material and the one or more citrate esters). The mixing can be performed using, for example, a melt extruder, a kneader extruder, a roll mill, a high shear mixer, a twin-screw compounder, or any other processing equipment known in the art. The conditions needed for the mixing are typically well known by those of skill in the art.

In one example mixing method, the polymeric material and the one or more citrate esters can be mixed in a predetermined weight ratio and then melt extruded. In another example, the polymeric material and the one or more citrate esters are mixed in a predetermined weight ratio and then formed into pellets. The pellets can be used in molding and/or extrusion processing methods to prepare a variety of articles.

Any suitable article can be formed from the mixture. Some example articles are molded objects prepared by processes such as injection molding, compression molding, or the like. Other example articles are fibers formed by spinning methods (e.g., melt spinning) or extrusion. Still other example articles are films prepared by casting from a solvent-containing mixture, by melt compression, by melt extrusion, or the like.

Some of the articles are adhesive articles. Stated differently, the compositions described herein can be adhesive compositions. The adhesive composition can be applied to a surface by melting the adhesive composition into a fluid state. For example, an adhesive layer can be formed on a substrate such as a tape backing by melt extrusion methods.

Extrusion methods tend to cause at least some alignment of the polymeric materials in the composition. This can lead to enhanced modulus from compositions that are extruded rather than solvent cast or compression molded. The modulus can be further enhanced by stretching in the machine direction. Stretching tends to cause further alignment of the polymeric material.

Polymeric films prepared from the compositions can have any desired thickness. The films are often visually clear. The can have a haze less than 5 percent, a transmittance equal to at least 90 percent, and a clarity equal to at least 90 percent using the Test Method 3 (Measurement of Total Transmittance, Haze, and Clarity) described in the Example section. The haze of such film samples is often less than 5 percent, less than 4 percent, less than 3 percent, less than 2 weight percent, or less than 1 weight percent. The transmittance and clarity are both often at least 92 percent, at least 94 percent at least 95 percent, at least 96 percent, at least 98 percent, or at least 99 percent. Low haze (e.g., less than 5 percent), high transmittance (e.g., greater than 90 percent), and high clarity (e.g., greater than 90 percent) are typically indicative of good compatibility between the polymeric material and the plasticizer (e.g., THF-citrate ester).

Some articles are prepared using a polymeric material that is a plant-based, that is a biodegradable, or both. For example, the polymeric material that is combined with the THF-citrate ester can be a cellulose-based material or a poly(lactic acid)-based material. Such compositions are often desired because both the plasticizer and the polymeric material can be obtained from plant rather than petroleum resources. Stated differently, these compositions can be considered to be environmentally friendly and can be derived from renewable resources.

Some traditional plasticizers (e.g., various phthalic acid esters such as diethyl phthalate) tend to migrate to the outer surface of the article and evaporate due to their relatively high volatility. When these traditional plasticizers evaporate from an article such as a polymeric film containing them, the article can have diminished flexibility compared to its initial flexibility. Additionally, other properties such as tensile strength, tear strength, and elongation to break can be adversely altered. Articles undergoing such changes tend to be characterized as exhibiting poor age stability.

In contrast to both phthatlic acid esters (e.g., diethyl phthalate) and commercially available tri(alkyl)-citrate esters (e.g., tri(alkyl)-citrate esters commercially available under the trade designation CITROFLEX from Vertellus (Greensboro, N.C., USA)), the THF-citrate esters tend to be less volatile and the articles containing them can have improved age stability. Stated differently, the THF-citrate esters can provide the same glass transition temperature reduction as many traditional plasticizers but can have improved age stability. The volatility of various plasticizers can be compared by monitoring the weight loss of compositions exposed to elevated temperatures. For example, the citrate esters can be heated at 100° C. for up to 96 hours with a weight loss of less than 2 weight percent, less than 1 weight percent, less than 0.8 weight percent, less than 0.6 weight percent, or less than 0.5 weight percent. Polymeric films made using the THF-citrates as plasticizers can have minimal or no loss of the plasticizer under normal use conditions.

Compared to many commonly used phthalate esters, the THF-citrate esters of Formula (I) tend to be more compatible with hydrophilic polymeric materials, tend to have a lower volatility, and tend to be more effective in lowering the glass transition temperature. Compared to many commercially available tri(alkyl)-citrate esters, the THF-citrate esters typically are somewhat more compatible with hydrophilic polymeric material, have a lower volatility, and are comparably effective in lowering the glass transition temperature.

Overall, the THF-citrate esters can be used advantageously as plasticizers for various polymeric materials including various renewable polymeric materials such as cellulose-based polymeric materials and poly(lactic acid)-based polymeric materials.

Various items are provided that are compositions and articles.

Item 1 is a composition that contains at least two different citrate esters of Formula (I).

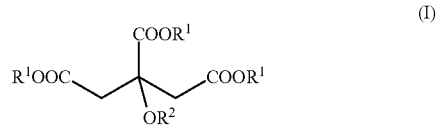

In Formula (I), each $R^1$ is an alkyl, tetrahydrofurfuryl group, or alkyl-substituted tetrahydrofurfuryl group, wherein at least one $R^1$ is a tetrahydrofurfuryl group or alkyl-substituted tetrahydrofurfuryl group; and $R^2$ is hydrogen or an acyl group.

Item 2 is the composition of item 1, wherein the composition further comprises a polymeric material.

Item 3 is the composition of item 2, wherein the polymeric material is prepared from renewable resources, is biodegradable, or both.

Item 4 is the composition of item 2 or 3, wherein the polymeric material is a thermoplastic polymer comprising an aliphatic polyester, a cellulose ester, polyvinyl chloride, or an acrylic polymer.

Item 5 is the composition of item 4, wherein the aliphatic polyester is a polylactic acid-based resin.

Item 6 is the composition of item 2 or 3, wherein the polymeric material is an elastomeric polymer.

Item 7 is the composition of any one of items 2 to 6, wherein the composition comprises 5 to 50 weight percent citrate esters of Formula (I) and 50 to 95 weight percent polymeric material based on a total weight of the composition.

Item 8 is an article comprising the composition of any one of items 2 to 7.

Item 9 is a composition that contains (a) at least one citrate ester of Formula (I)

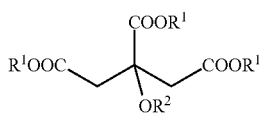

and at least one citrate ester of Formula (II).

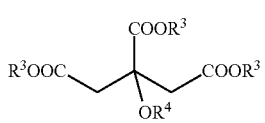

In Formula (I), each $R^1$ group is an alkyl, tetrahydrofurfuryl, or alkyl-substituted tetrahydrofurfuryl, wherein at least one $R^1$ is a tetrahydrofurfuryl or alkyl-substituted tetrahydrofurfuryl group. The $R^2$ group is hydrogen or an acyl. In Formula (II), each $R^3$ group is an alkyl and the $R^4$ group is hydrogen or an acyl.

Item 10 is the composition of item 9, wherein the composition further comprises a polymeric material Item 11 is the composition of item 10, wherein the polymeric material is prepared from renewable resources, is biodegradable, or both.

Item 12 is the composition of item 10 or 11, wherein the polymeric material is a thermoplastic polymer comprising an aliphatic polyester, a cellulose ester, polyvinyl chloride, or an acrylic polymer.

Item 13 is the composition of item 12, wherein the aliphatic polyester is a polylactic acid-based resin.

Item 14 is the composition of item 10 or 11, wherein the polymeric material is an elastomeric polymer.

Item 15 is the composition of any one of items 10 to 14, wherein the composition comprises 5 to 50 weight percent of the sum of citrate esters of Formula (I) plus the citrate ester of Formula (II) and 50 to 95 weight percent polymeric material based on a total weight of the composition.

Item 16 is an article comprising the composition of any one of items 10 to 15.

Item 17 is a composition that contains at least one citrate ester of Formula (III).

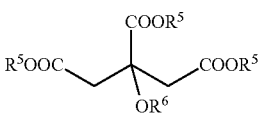

In Formula (III), each $R^5$ group is a tetrahydrofurfuryl or alkyl-substituted tetrahydrofurfuryl group. The $R^6$ group is hydrogen or an acyl.

Item 18 is the composition of item 17, wherein the composition further comprises a polymeric material.

Item 19 is the composition of item 18, wherein the polymeric material is prepared from renewable resources, is biodegradable, or both.

Item 20 is the composition of item 18 or 19, wherein the polymeric material is a thermoplastic polymer comprising an aliphatic polyester, a cellulose ester, polyvinyl chloride, or an acrylic polymer.

Item 21 is the composition of item 20, wherein the aliphatic polyester is a polylactic acid-based resin.

Item 22 is the composition of item 18 or 19, wherein the polymeric material is an elastomeric polymer.

Item 23 is the composition of any one of items 18 to 22, wherein the composition comprises 5 to 50 weight percent of the sum of citrate esters of Formula (I) plus the citrate ester of Formula (II) and 50 to 95 weight percent polymeric material based on a total weight of the composition.

Item 24 is an article comprising the composition of any one of items 18 to 23.

Item 25 is the article of any of the items 6, 16, or 24, wherein the compositions are adhesive compositions.

Item 26 is the article of item 25, wherein the adhesive composition is hot melt processable.

EXAMPLES

As used in the examples, all weights and percentages are by weight unless otherwise specified.

Acetic anhydride can be obtained from Sigma-Aldrich (Saint Louis, Mo., USA).

Acetone was obtained from VWR (West Chester, Pa., USA).

The alcohols isobutanol, n-butanol (1-butanol), and tetrahydrylfurfuryl alcohol, which is referred to as THF-alcohol, were obtained from Alfa Aesar (Ward Hill, Mass., USA).

Cellulose acetate was obtained from Eastman Chemical Company (Kingsport, Tenn., USA) under the trade designations CA-398-3 and CA-398-30. The number average molecular weights of CA-398-3 and CA-398-30 are 30,000 grams/mole and 50,000 grams/mole, respectively.

Tri(alkyl)citrate esters were obtained from Vertellus Performance Materials (Greensboro, N.C., USA) and/or Alfa Aesar (Ward Hill, Mass., USA) under the trade designation CITROFLEX 2 (triethyl citrate), CITROFLEX 4 (tri-n-butyl citrate), and CITROFLEX A-4 (acetyl tri-n-butyl citrate).

Citric Acid was obtained from Alfa Aesar (Ward Hill, Mass., USA).

Diethyl phthalate can be obtained from Sigma-Aldrich (Saint Louis, Mo., USA).

Ethyl acetate was obtained from VWR (West Chester, Pa., USA).

Methanesulfonic acid was obtained from Aldrich Chemical (Milwaukee, Wis., USA).

Poly(vinyl chloride) resin with a weight average molecular weight of about 62,000 grams/mole was obtained from Aldrich Chemical (Milwaukee, Wis., USA) as product number 18958-8.

Polylactic acid was obtained from Natureworks, LLC (Minnetonka, Minn., USA) under the trade designation PLA 4032D.

Test Methods

Test Method 1A: Determination of Glass Transition Temperature Using a Differential Scanning Calorimeter (DSC)

Approximately 5 to 7 milligrams of a polymer film sample was placed in an individual standard aluminum DSC pan with a lid, which can be obtained from TA Instruments (New Castle, Del., USA). The pan was then placed in the auto sampler of a Differential Scanning Calorimeter (Model Q2000 DSC from TA Instruments). For each analysis, the pan containing the sample was placed on one of the differential posts in the enclosed DSC cell along with an empty reference pan on the opposite post. Each sample was subjected to a heat-cool-heat profile over a temperature range of −20° C. to 250° C. The midpoint temperature (at the half height of the peak) of the glass transition peak was recorded as the glass transition temperature (Tg) during the second heating step of the profile.

Test Method 1B: Determination of Glass Transition Temperature Using a Differential Scanning Calorimeter (DSC)

A sample was tested in the same manner as for Test Method 1A except that the samples were subjected to a heat-cool-heat profile over a temperature range of −20° C. to 210° C.

Test Method 2: Measurement of Film Physical Properties

The percent elongation and modulus of the films were measured using a tensile testing machine commercially available as SINTECH from MTS Systems Corporation (Eden Prairie, Minn., USA). Specimens for this test were 2.54 centimeters wide and 15 centimeters long. An initial jaw separation of 5.1 centimeters and a crosshead speed of 12.7 centimeters per minute were used.

Test Method 3: Measurement of Total Transmittance, Haze, and Clarity

The films were measured for three optical parameters: percent luminous transmittance (total transmittance), haze and clarity using a haze-meter that is commercially available from BYK-Gardner USA (Columbia, Md., USA) under the trade designation HAZE-GARD PLUS (Model 4725). Sample specimens 15 centimeters by 15 centimeters in size were cut from film so that no oil, dirt, dust or fingerprints were present in the section to be measured. The specimens were then mounted by hand across the haze port of the haze-meter and the measurement activated. The optical parameters were measured and recorded. The total transmittance is indicated as "Trans" in the tables below.

Test Method 4: Measurement of Film Weight Loss

A 25 millimeter circle was die cut for each film sample and the initial weight recorded. Samples were placed in a 100° C. oven for 4, 24, 48 and 96 hours and the weight was recorded after removal from the oven. Samples were run in duplicate for each time and the weight loss percent was averaged.

Test Method 5: Gas Chromatographic Analysis

Approximately 100 milligrams (mg) of a product from a sample was weighed into a 100 milliliter (mL) volumetric flask. The sample was diluted to the 100 mL mark with dichloromethane. The sample was then placed into an auto-sampler vial and sealed with a Teflon coated cap. The sample was analyzed according to the conditions as follows:

GC Instrumental Parameters:
GC Instrument: Agilent 6890 Series with a 5973 MSD
Column: J & W DB-5 ms 30 meters by 320 micrometer by 1 micrometer
Program: Heat from 40° C. to 320° C. at 20° C./min; hold for 2 minutes at 320° C.
Gas Phase: Helium, 50 centimeters/second
Injection: 25 microliters, 20:1 split
Transfer line temp: 300° C.
Detection: EI Scan 14-650 Da GC peak areas ratios were determined to show the relative amounts of tri(THF citrate), di(THF)-mono(alkyl)-citrate, mono(THF)-di(alkyl)-citrate, and tri(alkyl)-citrate in the sample.

Test Method 6: Thermo-Gravimetric Analysis (TGA) of Citrate Esters

The weight loss of the citrate ester was measured by TGA. Approximately 30-50 milligrams of a sample was placed in a standard aluminum pan and heated to 500° C. at a rate of 10° C./min using a Model TGA 2950, which is commercially available from TA Instruments (New Castle, Del., USA). The weight loss of each sample was determined at 200° C. and 250° C.

Examples 1 to 4

Mixtures of tetrahydrofurfuryl alcohol (THF-alcohol), citric acid, 1-butanol (BuOH), methanesulfonic acid (MSA), and toluene were heated to reflux. The amounts of each component are shown in Table 1. The liberated water was collected in a Dean and Stark trap. After the reaction was complete (4-6 hours), the mixture was cooled and then washed with saturated aqueous sodium bicarbonate and brine. The organic layer was then concentrated under vacuum in a Roto-vaporizer. The crude product was then mechanically stirred and heated at 75° C. under high vacuum (0.8 millimeters Hg) to produce tetrahydrofurfuryl citrates as yellow or orange oils.

The ratios of products formed in Examples 1-4 were determined from gas chromatography according to Test Method 5. Results are shown in Table 2.

TABLE 1

Preparation of Citrate Esters PE-1-PE-4

| Example | THF-Alcohol (grams) | Citric Acid (grams) | BuOH (grams) | MSA (grams) | Toluene (mL) | Yield (grams) |
|---------|---------------------|---------------------|--------------|-------------|--------------|---------------|
| 1 | 146.68 | 80.00 | | 1.00 | 300 | 130.30 |
| 2 | 77.90 | 80.40 | 55.80 | 1.00 | 300 | 112.40 |
| 3 | 51.05 | 80.00 | 74.16 | 1.00 | 300 | 134.45 |
| 4 | 112.58 | 80.30 | 29.65 | 1.00 | 300 | 95.03 |

Example 5

The tri(THF)-citrate of Example 1 (20.34 grams, 45 mmoles), acetic anhydride (5.05 grams, 49 mmoles), and methanesulfonic acid (0.030 grams, 0.31 mmoles) were heated at 100° C. for 3 hours. The mixture was cooled, diluted with ethyl acetate (100 mL), and washed with saturated aqueous sodium bicarbonate. The organic layer was then concentrated under vacuum. The crude oil was purified by column chromatography over silica gel using a gradient of ethyl acetate in hexane (50% to 85%) to obtain the final product as a yellow oil (Yield 17.27 grams).

Example 6

A mixture of tetrahydrofurfuryl alcohol (585.70 grams, 5.7 moles), citric acid (600.00 grams, 3.1 moles), isobutanol (415.80 grams, 5.6 moles), methanesulfonic acid (5.00 grams, 52 mmoles), and toluene (1675 mL) were heated to reflux. The liberated water was collected in a Dean and Stark trap. After 11 hours, the mixture was cooled and then washed with saturated aqueous sodium bicarbonate. The organic layer was dried over magnesium sulfate and concentrated under vacuum in a Roto-vaporizer. The crude product was then stirred and heated at 80° C. under high vacuum (0.3 millimeters Hg) for 17 hours to produce a tetrahydrofurfuryl citrate as a yellow oil (Yield 934.58 grams). The relative amounts (percentage by weight of all the citrate esters in the example) of the products formed were determined using gas chromatography (Test Method 5) and are shown in Table 2.

TABLE 2

Relative Amounts of Products Formed

| Example | Tri(THF)-citrate | Di(THF)-mono(alkyl)-citrate | Mono(THF)-di(alkyl)-citrate | Tri(alkyl)-citrate |
|---|---|---|---|---|
| 1 | 100.0 | | | |
| 2 | 3.7 | 30.7 | 45.7 | 19.9 |
| 3 | 0.4 | 12.4 | 45.6 | 41.6 |
| 4 | 24.0 | 49.9 | 23.4 | 2.7 |
| 6 | 6.1 | 33.7 | 42.9 | 17.1 |

Thermogravimetric Analysis of Citrate Esters

The TGA method (Test Method 6) described above was used to analyze Examples 1-6. The results were compared to two commercially available tri(alkyl)-citrate esters (CITROFLEX 2 and CITROFLEX 4). The percent weight loss at 200° C. and 250° C. are shown in Table 3.

TABLE 3

Thermogravimetric Analysis of Citrate Esters

| Example | Weight loss at 200° C. (wt-%) | Weight loss at 250° C. (wt-%) |
|---|---|---|
| CITROFLEX 2 | 18.4 | 96.2 |
| CITROFLEX 4 | 14.3 | 79.5 |
| 1 | 1.4 | 2.4 |
| 2 | 5.1 | 17.7 |
| 3 | 5.1 | 28.3 |
| 4 | 2.3 | 10.6 |
| 5 | 2.3 | 7.0 |
| 6 | 3.4 | 15.0 |

Solubility Parameters

The solubility parameters of various citrate esters were determined from molecular dynamics simulations using the general procedures as described by Belmares et al., *J. Comp. Chem.*, 25 (15), 1814 (2004) and as implemented in CULGI Software that is commercially available from Culgi BV (P.O. Box 252, 2300 AG Leiden, The Netherlands). Results are shown in Table 4 and compared to the solubility parameter for polylactic acid as reported by Karst, D. and Yang, Y., *J. Appl. Poly. Sci.*, 96, 416-422 (2005).

TABLE 4

Solubility Parameters

| Material | Molecular Dynamics Solubility Parameter (cal/cc)$^{1/2}$ |
|---|---|
| Polylactic acid | 9.90 |
| Tri(ethyl)-citrate | 11.70 |
| Tri(butyl)-citrate | 8.87 |
| Example 1 | 11.10 |
| Di(THF)-mono(butyl)-citrate | 9.72 |
| Mono(THF)-di(butyl)-citrate | 9.32 |
| Example 5 | 9.30 |

Examples 7-11 and Comparative Examples C1-C5

Cellulose acetate compositions were each prepared by dissolving cellulose acetate (CA-398-30) in acetone at 20 percent by weight solids. The plasticizers shown in Table 5 were added to the composition in an amount to provide of 20 percent by weight of plasticizer based on the total solids composition (cellulose acetate and plasticizer). The compositions were mixed until homogeneous (about 1 hour). Films were prepared from each solution by knife coating the solution onto a 0.05 millimeters polypropylene carrier film. Each cast film was allowed to dry for 2 minutes at room temperature and then for 15 minutes in an oven set at 70° C. The dried films were removed from the carrier film after cooling to give a final thickness as indicated in Table 5.

Comparative examples C1-C5 were prepared without plasticizer (C1), with diethyl phthalate (C2), with CITROFLEX 2 (C3), with CITROFLEX 4 (C4), or with CITROFLEX A4 (C5).

The Tg for the films was determined according to Test Method 1A and total transmittance ("Trans"), haze, and clarity were determined according to Test Method 3. Results are shown in Table 5.

Examples 12-16 and Comparative Examples C6-C10

Cellulose acetate films were prepared and tested according to the procedure for Examples 7-11 and C1-C5 except that the cellulose acetate was CA-398-3. Results are shown in Table 5.

Examples 17-21 and Comparative Examples C11-C15

Cellulose acetate films were prepared and tested according to the procedure for Examples 7-11 and C1-C5 except that the cellulose acetate was a 50/50 mixture by weight of CA-398-3 and CA-398-30. Results are shown in Table 5.

TABLE 5

Optical Properties and Tg of Plasticized Cellulose Acetate Films

| Ex | Plasticizer | Plasticizer (wt-%) | Thickness (mm) | Trans (%) | Haze (%) | Clarity (%) | Tg (° C.) |
|---|---|---|---|---|---|---|---|
| C1 | None | 0 | 0.030 | 94.87 | 0.51 | 99.6 | 196 |
| C2 | Diethyl phthalate | 20 | 0.028 | 94.90 | 0.40 | 99.60 | 134 |
| C3 | CITROFLEX 2 | 20 | 0.034 | 94.93 | 0.40 | 99.63 | 134 |
| C4 | CITROFLEX 4 | 20 | 0.036 | 95.13 | 0.45 | 99.60 | 118 |
| C5 | CITROFLEX A4 | 20 | 0.035 | 94.90 | 10.42 | 99.40 | 163 |
| 7 | Example 1 | 20 | 0.034 | 95.03 | 0.39 | 99.30 | 141 |
| 8 | Example 2 | 20 | 0.039 | 95.03 | 0.45 | 99.63 | 140 |
| 9 | Example 3 | 20 | 0.044 | 94.77 | 0.50 | 99.43 | 137 |
| 10 | Example 4 | 20 | 0.037 | 94.73 | 0.35 | 99.63 | 134 |
| 11 | Example 5 | 20 | 0.030 | 94.93 | 0.59 | 99.50 | 140 |
| C6 | None | 0 | 0.032 | 94.87 | 0.99 | 99.47 | 191 |
| C7 | Diethyl phthalate | 20 | 0.034 | 94.53 | 0.67 | 99.60 | 123 |
| C8 | CITROFLEX 2 | 20 | 0.033 | 95.47 | 0.51 | 99.60 | 120 |
| C9 | CITROFLEX 4 | 20 | 0.035 | 95.13 | 0.47 | 99.63 | 125 |
| C10 | CITROFLEX A4 | 20 | 0.036 | 91.63 | 27.40 | 99.53 | 164 |
| 12 | Example 1 | 20 | 0.036 | 94.50 | 0.57 | 99.60 | 132 |
| 13 | Example 2 | 20 | 0.038 | 95.13 | 0.73 | 99.63 | 119 |
| 14 | Example 3 | 20 | 0.037 | 95.10 | 0.68 | 99.57 | 134 |
| 15 | Example 4 | 20 | 0.041 | 95.00 | 0.54 | 99.60 | 133 |
| 16 | Example 5 | 20 | 0.040 | 95.00 | 0.47 | 99.67 | 138 |
| C11 | None | 0 | 0.028 | 94.93 | 0.64 | 99.57 | 193 |
| C12 | Diethyl phthalate | 20 | 0.030 | 95.10 | 0.43 | 99.6 | 126 |
| C13 | CITROFLEX 2 | 20 | 0.030 | 94.97 | 0.40 | 99.67 | 126 |
| C14 | CITROFLEX 4 | 20 | 0.030 | 95.23 | 0.30 | 99.70 | 131 |

TABLE 5-continued

Optical Properties and Tg of Plasticized Cellulose Acetate Films

| Ex | Plasticizer | Plasticizer (wt-%) | Thickness (mm) | Trans (%) | Haze (%) | Clarity (%) | Tg (° C.) |
|---|---|---|---|---|---|---|---|
| C15 | CITRO-FLEX A4 | 20 | 0.030 | 92.33 | 13.63 | 99.57 | 163 |
| 17 | Example 1 | 20 | 0.030 | 95.07 | 0.42 | 99.70 | 133 |
| 18 | Example 2 | 20 | 0.030 | 94.47 | 0.40 | 99.70 | 127 |
| 19 | Example 3 | 20 | 0.030 | 95.23 | 0.63 | 99.60 | 134 |
| 20 | Example 4 | 20 | 0.030 | 95.10 | 0.40 | 99.63 | 137 |
| 21 | Example 5 | 20 | 0.030 | 95.20 | 0.36 | 99.63 | 137 |

Examples 22 and Comparative Examples C16-C17

Compositions were prepared by blending cellulose acetate (CA-398-30) with the plasticizer shown in Table 6 within an extruder hopper to provide a composition having 20 percent by weight plasticizer. Each composition was extruded through a twin screw extruder with a melt temperature of 230° C. and a die temperature set at 221° C. to provide a final film thickness as indicated in Table 6. Film samples were tested for total transmittance, haze, and clarity according to Test Method 3, and for physical properties according to Test Methods 1A and 2. Results are shown in Table 6.

TABLE 6

Properties of Extruded Plasticized Cellulose Acetate Films

| Ex | Plasticizer | Plasticizer (wt-%) | Thickness (mm) | Trans (%) | Haze (%) | Clarity (%) | Elongation (%) | Modulus (MPa) |
|---|---|---|---|---|---|---|---|---|
| C16 | Diethyl phthalate | 20 | 0.030 | 94.7 | 7.1 | 96.6 | 8 | 13 |
| C17 | CITRO-FLEX 2 | 20 | 0.034 | 94.7 | 0.7 | 99.4 | 6 | 15 |
| 22 | Example 1 | 20 | 0.041 | 94.2 | 0.8 | 99.4 | 4 | 39 |

Examples 23-31 and Comparative Examples C18-C19

Polylactic acid (PLA 4032D) was dried in an oven set at 80° C. for 2 hours. Compositions having 80 percent by weight polylactic acid and 20 percent by weight of a citrate ester plasticizer shown in Table 7 were compounded in a melt processor, which was a Brabender ATR Plasti-Corder from C.W. Brabender Instruments Company (Hackensack, N.J., USA), at a temperature of 200-210° C. with a mixing speed of 100 revolutions per minute (rpm).

Films were prepared by pressing 3.5 grams of the composition between two polyimide films in a hot press (Carver 2699, Carver Inc., USA) with 5 mil (0.127 millimeter) shims, a temperature setting of 200° C., and a clamp force of 24,000 pounds (10,886 kg). The thickness of each pressed film is shown in Table 7. The films were tested for total transmittance, haze, clarity, elongation at break, and modulus using Test Methods 2 and 3. These results are shown in Table 7. The glass transition temperatures were determined according to Test Methods 1B. The film weight loss was determined according to Test Method 4. Results are shown in Table 8.

TABLE 7

Properties of Plasticized PLA Films

| Ex | Plasticizer | Plasticizer (wt-%) | Thickness (mm) | Trans (%) | Haze (%) | Clarity (%) | Elongation (%) | Modulus (MPa) |
|---|---|---|---|---|---|---|---|---|
| C18 | None | 0 | | 95.0 | 2.9 | 95.3 | ND | ND |
| C19 | CITROFLEX 4 | 20 | 0.089 | 94.4 | 4.1 | 91.9 | 179 | 498 |
| 23 | Example 1 | 10 | 0.102 | 94.4 | 4.1 | 94.4 | ND | ND |
| 24 | Example 1 | 20 | 0.102 | 94.5 | 2.8 | 94.6 | 248 | 967 |
| 25 | Example 1 | 30 | 0.102 | 93.5 | 4.0 | 85.3 | ND | ND |
| 26 | Example 2 | 20 | 0.076 | 94.9 | 4.2 | 94.5 | 197 | 252 |
| 27 | Example 3 | 20 | 0.076 | 95.0 | 2.3 | 96.3 | 207 | 58 |
| 28 | Example 4 | 20 | 0.102 | 94.8 | 4.1 | 94.9 | 218 | 529 |
| 29 | CITROFLEX 4 & Example 1 (50/50 by wt) | 20 | 0.076 | 94.6 | 3.7 | 95.4 | 107 | 921 |
| 30 | Example 6 | 10 | ND | ND | ND | ND | ND | ND |
| 31 | Example 6 | 20 | ND | ND | ND | ND | ND | ND |

ND: Not determined

TABLE 8

Tg of Plasticizers and Weight Loss of Plasticized PLA Films

| | | | Film Weight Loss at 100° C. (wt-%) | | | |
|---|---|---|---|---|---|---|
| Ex | Plasticizer | Tg (° C.) | 4 hours | 24 hours | 48 hours | 96 hours |
| C18 | None | 63 | 0.05 | 0.06 | 0.02 | 0.05 |
| C19 | CITROFLEX 4 | 31 | 1.03 | 1.14 | 1.17 | 1.18 |
| 23 | Example 1 | 49 | 0.08 | ND | 0.10 | 0.11 |
| 24 | Example 1 | 39 | 0.14 | 0.17 | 0.21 | 0.23 |
| 25 | Example 2 | 20 | 0.20 | ND | ND | ND |
| 26 | Example 2 | 26 | 0.21 | 0.35 | 0.46 | 0.53 |
| 27 | Example 3 | 27 | 0.48 | 0.75 | 0.88 | 0.93 |
| 28 | Example 4 | 30 | 0.20 | 0.32 | 0.40 | 0.46 |
| 29 | CITROFLEX 4/ Example 1 (50/50 by wt) | 32 | 0.48 | 0.51 | 0.54 | 0.53 |
| 30 | Example 6 | 45 | ND | ND | ND | ND |
| 31 | Example 6 | 30 | ND | ND | ND | ND |

ND: Not determined

Examples 32-35 and Comparative Examples C20-C22

Polylactic acid (PLA 4032D) was placed in a dryer set at 65° C. for 24 hours prior to extrusion. Compositions were prepared by blending the dried PLA with the type and amount of plasticizer shown in Table 9. The compositions were then extruded through a twin screw extruder with a melt temperature of 176° C. and a die temperature of 176° C. Films with thickness ranging from 0.01 to 0.09 mm were obtained and film samples were tested for total transmittance, haze and clarity, elongation at break, and modulus using the methods described above. The glass transition temperatures were determined according to Test Method 1A. Results are shown in Table 9.

TABLE 9

Properties of Plasticized PLA Films

| Ex | Plasticizer | Plasticizer (wt-%) | Trans (%) | Haze (%) | Clarity (%) | Thickness (mm) | Elongation (%) | Modulus (MPa) | Tg, (° C.) |
|---|---|---|---|---|---|---|---|---|---|
| C20 | none | 0 | 94.2 | 1.2 | 99.2 | 0.064 | 5 | 1515 | 62.1 |
| C21 | CITROFLEX 2 | 20 | 94.2 | 3.5 | 97.2 | 0.076 | 222 | 661 | 37.3 |
| C22 | CITROFLEX 4 | 20 | 94.2 | 3.0 | 98.4 | 0.064 | 346 | 682 | 35.6 |
| 32 | Example 1 | 20 | 94.3 | 1.2 | 99.2 | 0.051 | 6 | 2150 | 39.7 |
| 33 | Example 1 | 12 | 94.8 | 0.8 | 99.2 | 0.064 | 5 | 2179 | 50.6 |
| 34 | Example 2 | 20 | 94.4 | 3.2 | 97.9 | 0.089 | 291 | 992 | 33.0 |
| 35 | Example 2 | 12 | 94.1 | 0.7 | 98.9 | 0.013 | 34 | 1603 | 40.0 |

Examples 36-38 and Comparative Examples C23-C24

The PLA melt extruded film samples were oriented, i.e., stretched, both in the machine direction (MD) and cross direction (CD). Film samples were cut into 63.5 mm×63.5 mm squares. Each film was placed in a KARO IV Laboratory Stretching Machine (Brueckner Technology Holding, Germany), heated to 55° C. for 30 seconds, stretched at a speed of 31.8 mm/second, and then annealed at 55° C. to obtain films having a ratio of 101.6 mm×101.6 mm. The films were tested in both machine direction (MD) and cross direction (CD) for physical properties according to Test Method 2. Results are shown in Table 10.

TABLE 10

Physical Properties of Oriented and Plasticized PLA Films

| Ex | Film Example | Thickness (mm) | Elongation MD (%) | Modulus MD (MPa) | Elongation CD (%) | Modulus CD (MPa) |
|---|---|---|---|---|---|---|
| C23 | C21 | 0.025 | 116 | 452 | 33 | 856 |
| C24 | C22 | 0.025 | 98 | 1028 | 73 | 956 |
| 36 | 32 | 0.127 | 66 | 3114 | 30 | 2449 |
| 37 | 34 | 0.025 | 34 | 1603 | 8 | 2116 |
| 38 | 35 | 0.025 | 6 | 2077 | 4 | 1781 |

Examples 39-42 and Comparative Example C25

Mixtures of PVC (poly(vinyl chloride)), plasticizer, and tetrahydrofuran in amounts shown in Table 10 were shaken for 12 hours at room temperature. Approximately 5.0 grams of each solution was poured into an aluminum pan and dried under vacuum (0.5 millimeters Hg) at room temperature for 24 hours. Comparative Example 25 contains only PVC (no plasticizer was added). All samples were transparent films. The glass transition temperature of each sample was determined according to Test Method 1B and is shown in Table 11.

TABLE 11

Plasticized Poly(vinyl chloride) compositions and Tg

| Ex | Plasticizer | Plasticizer (grams) | PVC (grams) | Tetrahydrofuran (grams) | Tg (° C.) |
|---|---|---|---|---|---|
| C25 | None | | | | 81 |
| 39 | Example 1 | 0.50 | 4.50 | 20.80 | 47 |
| 40 | Example 1 | 1.01 | 4.00 | 21.82 | 33 |
| 41 | Example 3 | 0.51 | 4.50 | 19.42 | 47 |
| 42 | Example 3 | 1.00 | 4.00 | 20.91 | 17 |

What is claimed is:

1. A composition comprising:
   a) at least two different citrate esters of Formula (I)

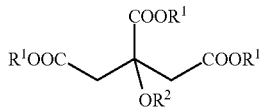

(I)

wherein
   each $R^1$ is an alkyl, tetrahydrofurfuryl group, or alkyl-substituted tetrahydrofurfuryl group, wherein at least one $R^1$ is a tetrahydrofurfuryl group or alkyl-substituted tetrahydrofurfuryl group; and
   $R^2$ is hydrogen or an acyl group.

2. The composition of claim 1, wherein the composition further comprises a polymeric material.

3. The composition of claim 2, wherein the polymeric material is a thermoplastic polymer that is an aliphatic polyester, a cellulose ester, polyvinyl chloride, or an acrylic polymer.

4. The composition of claim 2, wherein the polymeric material is an elastomeric polymer.

5. The composition of claim 2, wherein the composition comprises 5 to 50 weight percent citrate esters of Formula (I) and 50 to 95 weight percent polymeric material based on a total weight of the composition.

6. An article comprising the composition of claim 2.

7. A composition comprising:
   a) at least one citrate ester of Formula (I)

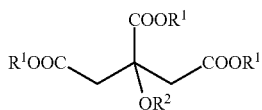

(I)

wherein
   each $R^1$ is an alkyl, tetrahydrofurfuryl group, or alkyl-substituted tetrahydrofurfuryl group, wherein at least one $R^1$ is a tetrahydrofurfuryl group or alkyl-substituted tetrahydrofurfuryl group; and
   $R^2$ is hydrogen or an acyl group; and
   b) at least one citrate ester of Formula (II)

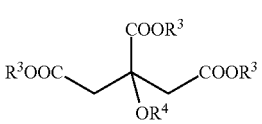

(II)

wherein
   each $R^3$ is an alkyl; and
   $R^4$ is hydrogen or an acyl group.

8. The composition of claim 7, wherein the composition further comprises a polymeric material.

9. The composition of claim 8, wherein the polymeric material is a thermoplastic polymer comprising an aliphatic polyester, a cellulose ester, polyvinyl chloride, or an acrylic polymer.

10. The composition of claim 8, wherein the polymeric material is an elastomeric polymer.

11. The composition of claim 8, wherein the composition comprises 5 to 50 weight percent of the sum of citrate esters of Formula (I) plus the citrate ester of Formula (II) and 50 to 95 weight percent polymeric material based on a total weight of the composition.

12. An article comprising the composition of claim 8.

13. The composition of claim 1, wherein one of the citrate esters of Formula (I) is the following Formula (III):

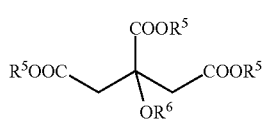

(III)

wherein
   each $R^5$ is tetrahydrofurfuryl group or alkyl-substituted tetrahydrofurfuryl group; and
   $R^6$ is hydrogen or an acyl.

14. The composition of claim 7, wherein the compound of Formula (I) is the following Formula (III):

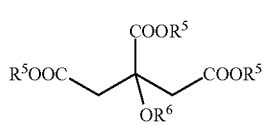

(III)

wherein
   each $R^5$ is tetrahydrofurfuryl group or alkyl-substituted tetrahydrofurfuryl group; and
   $R^6$ is hydrogen or an acyl.

15. The composition of claim 14, wherein the composition further comprises a polymeric material.

16. An article comprising the composition of claim 15.

* * * * *

UNITED STATES PATENT AND TRADEMARK OFFICE
CERTIFICATE OF CORRECTION

Page 1 of 2

PATENT NO.        : 9,670,335 B2
APPLICATION NO.   : 14/387596
DATED             : June 6, 2017
INVENTOR(S)       : Maureen Kavanagh et al.

It is certified that error appears in the above-identified patent and that said Letters Patent is hereby corrected as shown below:

In the Specification

Column 3
Lines 32-33 (approx.), delete "tetrahydrofurfurtyl" and insert -- tetrahydrofurfuryl --, therefor.

Column 8
Line 47, delete "hydroxypropanic" and insert -- hydroxypropionic --, therefor.

Column 9
Lines 15-16 (approx.), delete "hydroxypropanic" and insert -- hydroxypropionic --, therefor.
Line 17, delete "hydropentanoic" and insert -- hydroxypentanoic --, therefor.

Column 10
Line 4, delete "tributryrate" and insert -- tributyrate --, therefor.
Line 18, delete "proprionate" and insert -- propionate --, therefor.

Column 12
Line 47, delete "trimettitate" and insert -- trimellitate --, therefor.
Line 48, delete "trimettilate" and insert -- trimellitate --, therefor.
Line 49, delete "trimettilate" and insert -- trimellitate --, therefor.

Column 13
Line 61, delete "phthatlic" and insert -- phthalic --, therefor.

Column 15
Line 25, after "material" insert -- . --.

Signed and Sealed this
Fifteenth Day of August, 2017

Joseph Matal
*Performing the Functions and Duties of the*
*Under Secretary of Commerce for Intellectual Property and*
*Director of the United States Patent and Trademark Office*

Column 16
Lines 24-25 (approx.), delete "tetrahydrylfurfuryl" and insert -- tetrahydrofurfuryl --, therefor.

Column 18
Line 7, delete "tetahydrofurfuryl" and insert -- tetrahydrofurfuryl --, therefor.